(12) United States Patent
DeWaard

(10) Patent No.: US 10,611,700 B2
(45) Date of Patent: Apr. 7, 2020

(54) SELF-FLUSHING ANAEROBIC DIGESTER SYSTEM

(71) Applicant: Daritech, Inc., Lynden, WA (US)

(72) Inventor: David DeWaard, Lynden, WA (US)

(73) Assignee: Dari-Tech, Inc., Lynden, WA (US)

( * ) Notice: Subject to any disclaimer, the term of this patent is extended or adjusted under 35 U.S.C. 154(b) by 155 days.

(21) Appl. No.: 15/479,640

(22) Filed: Apr. 5, 2017

(65) Prior Publication Data
US 2017/0283338 A1 Oct. 5, 2017

Related U.S. Application Data

(60) Provisional application No. 62/318,705, filed on Apr. 5, 2016.

(51) Int. Cl.
*C12M 1/107* (2006.01)
*C05F 17/02* (2006.01)
*C05F 17/00* (2020.01)
*C05F 1/00* (2006.01)
(Continued)

(52) U.S. Cl.
CPC .......... *C05F 17/0276* (2013.01); *C05F 1/007* (2013.01); *C05F 17/0018* (2013.01); *C05F 17/0045* (2013.01); *C05F 17/0054* (2013.01); *C05F 17/027* (2013.01); *C12M 21/04* (2013.01); *C12M 23/58* (2013.01); *C12M 33/12* (2013.01); *Y02A 40/201* (2018.01); *Y02E 50/343* (2013.01);
(Continued)

(58) Field of Classification Search
CPC ...................................................... C12M 21/04
See application file for complete search history.

(56) References Cited

U.S. PATENT DOCUMENTS

| 1,493,091 A | 5/1924 | Wiggins |
| 1,693,857 A | 12/1928 | Moser |
| 1,716,491 A | 6/1929 | Griffin |

(Continued)

FOREIGN PATENT DOCUMENTS

| CA | 2336838 | 3/2005 |
| CA | 2690420 A1 | 7/2010 |

(Continued)

OTHER PUBLICATIONS

FR2872676A1, Google Machine Translation, 2015, 20 pages.
Nazaroff & Alvarez-Cohen, Anaerobic Digestion of Wastewater Sludge, Jan. 12, 2017, 7 pages.

*Primary Examiner* — William H. Beisner
(74) *Attorney, Agent, or Firm* — Williams, Kastner & Gibbs PLLC; Mark Lawrence Lorbiecki

(57) ABSTRACT

A digester system comprising a primary digester tank containing a primary feed material portion, a secondary digester tank containing a secondary feed material portion, a first conduit connected between the primary digester tank and the secondary digester tank to define a primary tank lower opening within the primary digester tank and a secondary digester tank lower opening within the secondary digester tank, and a flow control valve configured to allow or prevent flow of fluid through the first conduit. When the flow control valve is configured to allow flow of fluid through the first conduit, a portion of the primary feed material portion flows from the primary digester tank to the secondary digester tank to form the secondary feed material portion.

14 Claims, 7 Drawing Sheets

(51) Int. Cl.
*C12M 1/26* (2006.01)
*C12M 1/00* (2006.01)

(52) U.S. Cl.
CPC .............. *Y02P 20/145* (2015.11); *Y02W 30/43* (2015.05); *Y02W 30/47* (2015.05)

(56) References Cited

U.S. PATENT DOCUMENTS

| | | | |
|---|---|---|---|
| 2,041,318 A | 5/1936 | Berger | |
| 2,056,857 A | 10/1936 | Inboden et al. | |
| 2,497,047 A | 2/1950 | Prager et al. | |
| 2,497,645 A | 2/1950 | Wiggins | |
| RE23,417 E | 10/1951 | Prager et al. | |
| 2,722,357 A | 11/1955 | Whitecar | |
| 2,789,722 A | 4/1957 | Oberst | |
| 2,808,958 A | 10/1957 | Wiggins | |
| 2,844,169 A | 7/1958 | Skinner | |
| 2,948,593 A | 8/1960 | Larson | |
| 3,041,148 A | 6/1962 | Ballantyne et al. | |
| 3,074,587 A | 1/1963 | Jennings | |
| 3,158,667 A | 11/1964 | Michaels | |
| 3,178,267 A | 4/1965 | Larson | |
| 3,251,471 A | 5/1966 | Allen | |
| 3,535,236 A | 10/1970 | Travis | |
| 3,535,712 A | 10/1970 | Zeff et al. | |
| 3,676,074 A | 7/1972 | Shibayama et al. | |
| 3,679,053 A | 7/1972 | James et al. | |
| 3,874,175 A | 4/1975 | Winters | |
| 3,922,514 A | 11/1975 | Greenhut | |
| 3,950,249 A | 4/1976 | Eger et al. | |
| 3,952,421 A | 4/1976 | Wilson et al. | |
| 4,154,685 A | 5/1979 | Marcotte | |
| 4,342,383 A | 8/1982 | Burnett | |
| 4,419,550 A | 12/1983 | Monette | |
| 4,437,987 A * | 3/1984 | Thornton | C02F 3/28 210/137 |
| 4,473,467 A | 9/1984 | Marcotte | |
| 4,633,535 A | 1/1987 | Louvo | |
| 4,836,918 A | 6/1989 | Szikriszt | |
| 5,033,863 A | 7/1991 | Linkletter | |
| 5,292,637 A | 3/1994 | Bohnensieker | |
| 5,300,438 A | 4/1994 | Augspurger et al. | |
| 5,357,855 A | 10/1994 | Ishigaki et al. | |
| 5,407,809 A | 4/1995 | Finn | |
| 5,409,610 A | 4/1995 | Clark | |
| 5,534,437 A | 7/1996 | Arrau | |
| 5,586,731 A | 12/1996 | Glaze et al. | |
| 5,589,391 A | 12/1996 | Fink | |
| 5,593,888 A | 1/1997 | Glaze et al. | |
| 5,618,424 A | 4/1997 | Nagaoka | |
| 5,661,031 A | 8/1997 | Murphy et al. | |
| 5,716,013 A | 2/1998 | Benson et al. | |
| 5,759,850 A | 6/1998 | Seymour | |
| 5,776,768 A | 7/1998 | Seymour et al. | |
| 5,887,908 A | 3/1999 | White | |
| 5,922,094 A | 7/1999 | Richards | |
| 5,925,561 A | 7/1999 | Posselius, Jr. et al. | |
| 6,056,800 A | 5/2000 | Carter, IV | |
| 6,105,536 A | 8/2000 | DeWaard | |
| 6,281,001 B1 | 8/2001 | McNelly | |
| 6,397,492 B1 | 6/2002 | Malley | |
| 6,443,094 B1 | 9/2002 | DeWaard | |
| 6,454,944 B1 * | 9/2002 | Raven | C12M 21/04 210/180 |
| 6,783,975 B2 | 8/2004 | Windle | |
| 6,997,135 B1 | 2/2006 | DeWaard | |
| 7,056,441 B1 | 6/2006 | Menke et al. | |
| 7,138,271 B2 | 11/2006 | Pratte | |
| 7,270,754 B2 | 9/2007 | Menke et al. | |
| 7,306,731 B1 | 12/2007 | DeWaard | |
| 7,468,132 B2 | 12/2008 | Zotter et al. | |
| 7,615,155 B1 * | 11/2009 | Hansen | B09B 3/00 210/603 |
| 7,631,595 B1 | 12/2009 | DeWaard | |
| 7,708,885 B2 | 5/2010 | Lanting et al. | |
| 7,721,903 B2 | 5/2010 | Ben Afeef | |
| 7,987,778 B1 | 8/2011 | DeWaard | |
| 8,142,667 B2 | 3/2012 | DeWaard | |
| 8,201,495 B2 | 6/2012 | DeWaard | |
| 9,422,181 B1 | 8/2016 | Borchard et al. | |
| 9,751,787 B1 | 9/2017 | DeWaard | |
| 2001/0040131 A1 | 11/2001 | Yamane | |
| 2002/0006075 A1 | 1/2002 | Ferris et al. | |
| 2005/0089998 A1 | 4/2005 | Miller | |
| 2006/0154362 A1 | 7/2006 | Sundberg | |
| 2008/0093292 A1 | 4/2008 | Zotter et al. | |
| 2008/0277336 A1 | 11/2008 | Dvorak | |
| 2009/0065448 A1 | 3/2009 | Schedler | |
| 2009/0200231 A1 | 8/2009 | Walton et al. | |
| 2009/0249685 A1 | 10/2009 | Flowers et al. | |
| 2010/0112632 A1 | 5/2010 | DeWaard | |
| 2011/0100930 A1 | 5/2011 | DeWaard | |
| 2011/0198268 A1 | 8/2011 | DeWaard | |
| 2011/0253227 A1 | 10/2011 | DeWaard | |
| 2011/0309039 A1 | 12/2011 | DeWaard | |
| 2012/0000863 A9 | 1/2012 | DeWaard | |
| 2012/0058534 A1 * | 3/2012 | Stover | C02F 3/006 435/167 |
| 2012/0138515 A1 | 6/2012 | DeWaard | |
| 2015/0001145 A1 | 1/2015 | Monsrreal | |
| 2015/0090649 A1 | 4/2015 | Crompton | |
| 2016/0348054 A1 | 12/2016 | Shi et al. | |

FOREIGN PATENT DOCUMENTS

| | | | | |
|---|---|---|---|---|
| CA | 2719630 A1 | 5/2011 | | |
| CA | 2732065 A1 | 8/2011 | | |
| CA | 2737609 A1 | 10/2011 | | |
| CA | 2764679 A1 | 7/2012 | | |
| GB | 818010 A | * | 8/1959 | ............. B01D 21/18 |
| GB | 1414829 A | * | 11/1975 | ........... B01D 21/245 |
| WO | 2010094115 A1 | 8/2010 | | |

* cited by examiner

SELF-FLUSHING ANAEROBIC DIGESTER SYSTEM

RELATED APPLICATIONS

This application, U.S. patent application Ser. No. 15/479,640 filed Apr. 5, 2017 claims benefit of U.S. Provisional Application Ser. No. 62/318,705 filed Apr. 5, 2016, the contents of which are incorporated herein by reference.

TECHNICAL FIELD

The present invention relates to digester systems and methods and, in particular, to systems and methods for removing non-digestible solids form a digester tank of a digester system without substantially disrupting operation of the digester system.

BACKGROUND

Anaerobic digester systems and methods employ microorganisms to break down biodegradable material in the absence of oxygen. The present invention is of particular significance when the biodegradable material is animal waste from a diary facility, and that example of the present invention will be described herein in detail. However, the principles of the present invention may be applied to other types of biodegradable material and other operating environments.

An anaerobic digester system conventionally comprises a sealed digester tank in which feed material is contained during the anaerobic digestion process. During the anaerobic digestion processes, microorganisms break the feed material down into biogas and digestate. The biogas is removed from the digester tank and may be used as an energy source. The digestate is nutrient rich and may be used as a fertilizer.

When the biodegradable material is animal waste from a dairy facility, the biodegradable material is combined with fluid to facilitate transport and processing of the biodegradable material. Further, solid contaminates (e.g., non-digestible solids such as sand) may be entrained by the fluids used to convey the biodegradable material. The term "raw feed material" will be used to describe the slurry of biodegradable material, fluids, and solid and other contaminates introduced into the digester tank of a digester system.

During the anaerobic digestion process, the feed material within digester tank is largely undisturbed. Heavier solid contaminates within the digester tank, such as sand, thus settle to the bottom of the tank. Settled contaminates can interfere with proper functioning of the anaerobic digestion process and should be removed. Conventionally, contaminates in the raw feed material are periodically removed by emptying the tank and cleaning the settled contaminates from the bottom of the tank.

The need exists for anaerobic digestion systems and methods capable of removing at least a portion of settled solid contaminates from the digesting tank without disrupting the anaerobic digestion process.

SUMMARY

The present invention may be embodied as a digester system comprising a primary digester tank, a secondary digester tank, a first conduit, and a flow control valve. The primary digester tank contains a primary feed material portion defining a primary feed material level. The secondary digester tank contains a secondary feed material portion defining a secondary feed material level. The first conduit is connected between the primary digester tank and the secondary digester tank to define a primary tank lower opening within the primary digester tank and a secondary digester tank lower opening within the secondary digester tank. The primary digester tank lower opening is below the primary feed material level and the secondary digester tank lower opening is below the secondary feed material level. The flow control valve is configured to allow or prevent flow of fluid through the first conduit. When the flow control valve is configured to allow flow of fluid through the first conduit, a portion of the primary feed material portion flows from the primary digester tank to the secondary digester tank to form the secondary feed material portion.

The present invention may be embodied as a digester system comprising a primary digester tank, a secondary digester tank, a first conduit, a second conduit, and a flow control valve. The primary digester tank contains a primary feed material portion defining a primary feed material level. The secondary digester tank contains a secondary feed material portion defining a secondary feed material level. The first conduit is connected between the primary digester tank and the secondary digester tank to define a primary tank lower opening within the primary digester tank and a secondary digester tank lower opening within the secondary digester tank, where the primary digester tank lower opening is below the primary feed material level and the secondary digester tank lower opening is below the secondary feed material level. The second conduit is connected between the primary digester tank and the secondary digester tank to define a primary tank upper opening within the primary digester tank and a secondary digester tank upper opening within the secondary digester tank, where the primary digester tank upper opening is above the primary feed material level and the secondary digester tank upper opening is above the secondary feed material level. The flow control valve is configured to allow or prevent flow of fluid through the second conduit. The pump is operatively connected to the secondary digester tank and a separator. When the flow control valve is configured to allow flow of fluid through the first conduit, a portion of the primary feed material portion flows at a first flow rate from the primary digester tank to the secondary digester tank to form the secondary feed material portion. The pump is configured to transfer at least a portion of the secondary feed material portion from the secondary digester tank to the separator at a second flow rate. The first flow rate is greater than the second flow rate. The separator separates the secondary feed material portion pumped from the secondary digester tank into liquid and solid components.

The present invention may also be embodied as an anaerobic digesting method comprising the following steps. A primary digester tank is provided. A primary feed material portion defining a primary feed material level is within the primary digester tank. A secondary digester tank is provided. A first conduit is connected between the primary digester tank and the secondary digester tank to define a primary tank upper opening within the primary digester tank and a secondary digester tank upper opening within the secondary digester tank such that the primary digester tank upper opening is below the primary feed material level and the secondary digester tank upper opening is below the secondary feed material level. A flow control valve is configured to allow or prevent flow of fluid through the first conduit. The flow control valve is configured to allow flow of fluid through the first conduit such that a portion of the primary feed material portion flows at a first flow rate from the primary digester tank to the secondary digester tank to form a secondary feed material portion. At least a portion of the secondary feed material portion is transferred from the secondary digester tank at a second flow rate, where the first flow rate is greater than the second flow rate.

DETAILED DESCRIPTION

The present invention may be embodied in different forms, and two examples of anaerobic digester systems constructed in accordance with, and embodying, the principles of the present invention will be described below.

I. First Example Anaerobic Digester System

Figure 1:
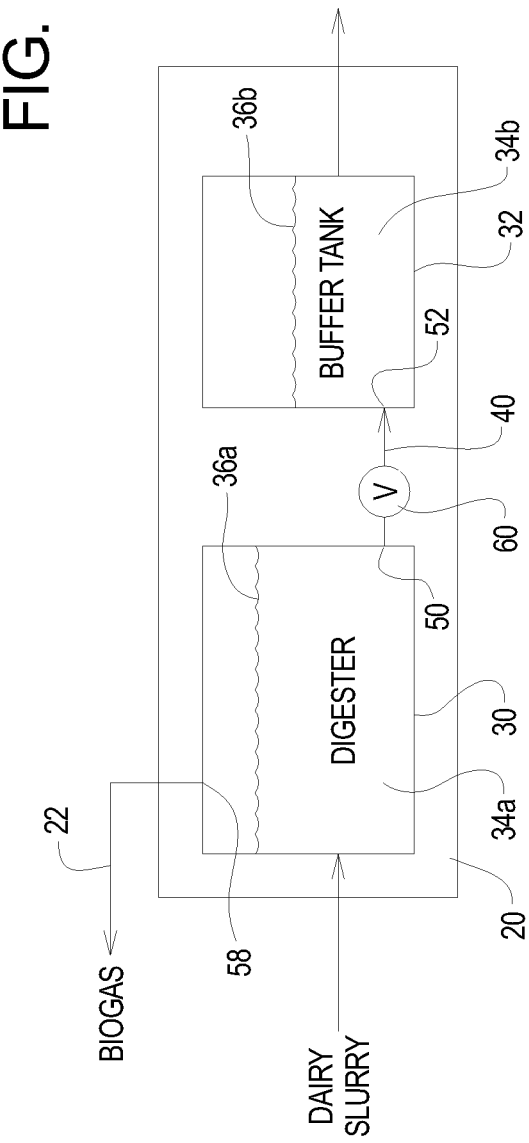
FIG. 1 is a schematic diagram of a first example anaerobic digester system of the present invention.

Referring initially to FIG. 1 of the drawing, depicted therein is a first example anaerobic digester system 20. FIG. 1 further illustrates that that biogas is removed from the digester system through a biogas conduit 22. The first example anaerobic digester system 20 may be used with a separator (not shown) for separating separator feed material into dry solids and liquids, and the liquids may be directed to a long term storage lagoon or the like (not shown).

As shown in FIG. 1, the first example anaerobic digester system 20 comprises a primary digester tank 30 and a secondary or buffer digester tank 32. A primary feed material portion 34a being processed by the example digester system 20 is within the primary digester tank 30 as shown in FIG. 1. The primary feed material portion 34a within the primary digester tank 30 defines a primary feed material level 36a. FIG. 1 also illustrates that a secondary feed material portion 34b is within the secondary digester tank 32, and the secondary feed material portion 34b within the secondary digester tank 32 defines a secondary feed material level 36b.

A first conduit 40 connects the primary digester tank 30 to the secondary digester tank 32. In particular, the first conduit 40 is configured to define a digester tank lower opening 50 and a secondary tank lower opening 52. The first conduit 40 is arranged such that the primary tank lower opening 50 and secondary tank lower opening 52 are within the primary and secondary digester tanks 30 and 32 below the primary feed material level 36a and secondary feed material level 36b, respectively. The biogas conduit 22 defines a biogas opening 58 through which biogas passes from the primary digester tank 30 into the biogas conduit 22, and the biogas opening 58 is also above the primary feed material level 36a. Further, for reasons that will be explained in further detail below, the primary tank lower opening 50 is arranged at or near a bottom of the interior of the primary tank 30.

FIG. 1 further illustrates that a flow control valve 60 is arranged to control flow of fluid through the first conduit 40. The flow control valve 60 operates in a closed configuration and at least one open configuration. Typically, the flow control valve 60 may operate in a continuum of open configurations between the closed configuration and a fully open configuration. In the closed configuration, the flow control valve 60 prevents flow of fluid through the first conduit 40. In any open configuration, the flow control valve 60 allows fluid flow between the primary digester tank 30 and the secondary digester tank 32 through the first conduit 40.

The first example anaerobic digester system 20 operates generally as follows. The primary feed material 34a is introduced into the primary digester tank 30. The primary digester tank 30 is operated in a conventional manner to generate biogas and digestate. The biogas is removed from the primary digester tank 30 through the biogas opening 58 and the biogas conduit 22.

The primary digester tank 30 is sized and dimensioned relative to the secondary digester tank 32 such that the head pressure within the primary digester tank 30 is much greater than the head pressure within the secondary digester tank 32. Periodically, a portion of the primary feed material 34a comprising the digestate, liquid material, and solid contaminate (such as sand) is allowed to flow at a first, relatively high, flow rate from the primary digester tank 30 into the secondary digester tank 32. In particular, a portion of the primary feed material 34a flows through the first conduit 40 and the flow control valve 60 and into the secondary digester tank 32 to form the secondary feed material 34b. The first conduit 40 and flow control valve 60 are sized, dimensioned, and/or controlled such that the head pressure within the primary digester tank 30 forces a portion of the secondary feed material 34a from the primary digester tank 30 to the secondary digester tank 32 at the first flow rate (e.g., 6000 gpm) for a short flush time period.

The flush time duration depends on factors such as the relative sizes of the primary digester tank 30 and secondary digester tank 32, the size of the first conduit 40, and the nature of the feed material. The flush time duration should be sufficient to flush feed material having a relatively high concentration of solid contaminate from the primary digester tank 30. However, the flush time duration should be kept short enough such that primarily feed material with a relatively high concentration of solid contaminate is removed from the primary digester tank 30. The valve 60 is configured to be fully open for a flush time duration within a first range of approximately 10-15 seconds or a second range of approximately 5-20 seconds. Because they type of valve use as the example valve 60 (e.g., butterfly valve) may take from 3-5 seconds to open, the total time from initiation of the flush process to cessation of the flush process may be in a first range of 16-25 seconds or a second range of 11-30 seconds.

The location of the primary tank lower opening 50 is arranged and the first flow rate selected such that the solid contaminate that has accumulated at the bottom of the primary digester tank 30 is flushed out of the primary digester tank 30 along with some digestate and liquid material. Accordingly, the secondary feed material 34b within the secondary digester tank 32 typically contains a much higher percentage of solid contaminate than the primary feed material 34a within the primary digester tank 30.

The anaerobic digestion process continues to act on the secondary feed material 34b in the secondary digester tank 32. At the same time, the secondary feed material 34b may be periodically or continuously removed from the secondary digester tank 32 at a second, relatively low, flow rate (e.g., 50 gpm). The removed secondary feed material 34b may be further separated into dry solids and liquids. Any digestate in the removed secondary feed material 34b forms at least a part of the dry solids and may be removed from contaminate and used or otherwise safely disposed of.

Solid contaminate, especially non-digestible, relatively dense solids such as sand, will thus be carried by the intense, short duration flow of feed material from the primary digester tank 30 to the secondary digester tank 32. In particular, non-digestible solids that are more dense than the liquids (primarily water) forming the primary feed material 34a will sink to the bottom of the primary digester tank 30 such that such solid contaminates, and especially non-digestible, relatively dense solid contaminates such as sand, are relatively highly concentrated within the bottom of the primary digester tank 30. The primary feed material 34a flushed from the primary digester tank 30 and into the secondary digester tank 32 through the first conduit 40 and the flow control valve 60 will thus contain a higher concentration of solid contaminates than the primary feed material 34a that remains within the primary digester tank 30.

Accordingly, by periodically removing a relatively small amount of primary feed material 34a with a high concentration of solid contaminate, especially non-digestible, relatively dense solids such as sand, from the primary digester tank 30, the primary digester tank 30 is continually cleaned and thus allowed to operate at a relatively high level of efficiency in comparison to a digester system not having a secondary digester tank 32.

The following discussion defines certain characteristics of the first example anaerobic digester system 20. In particular, Table A defines characteristics defining the first flow rate and the relationship of the first flow rate to the second flow rate. The text following Table A generally describes the relationship between the respective volumes of the first and second digester tanks 30 and 32, the typical size and dimensions of the second digester tank 32, the cross-sectional area of the first conduit 40, and the frequency and length of the flush time duration.

TABLE A

| Characteristic | Example | First Preferred Range | Second Preferred Range |
| --- | --- | --- | --- |
| First Flow Rate | 6000 gpm | 5000-7000 gpm | 2000-20000 gpm |
| Second Flow Rate | 50 gpm | 25-100 gpm | 10-1000 gpm |
| Ratio of First to Second Flow Rate | 120:1 | 50-280:1 | 2-2000:1 |
| Secondary Conduit Diameter | 4" | 3-5" | 2-10" |

The volume of the primary digester tank 30 can vary significantly depending upon the requirements of a particular installation, with the volume of the primary digester tank 30 potentially being as large as a million (1,000,000) gallons. The volume of the secondary digester tank 32 need not scale linearly with the volume of the primary digester tank 30. As the volume of the primary digester tank 30 is scaled up, the frequency and possibly flush time duration, rather than the size of the secondary digester tank, may be increased to handle larger volume primary digester tanks.

Typically, the diameter of the secondary digester tank 32 will be in the range of from four to eight feet (4-8'). The height of the secondary digester tank 32 is, at a minimum, sufficient to provide sufficient volume within the secondary tank 32 to handle the short burst of feed material flushed from the primary digester tank 30. In addition, the height of the secondary digester tank 32 is typically selected to be approximately at least as tall as the height of the primary digester tank 30 such that failure of the valve 60 will simply fill up, but not overflow, the secondary digester tank 32.

II. Second Example Anaerobic Digester System

Figure 2:
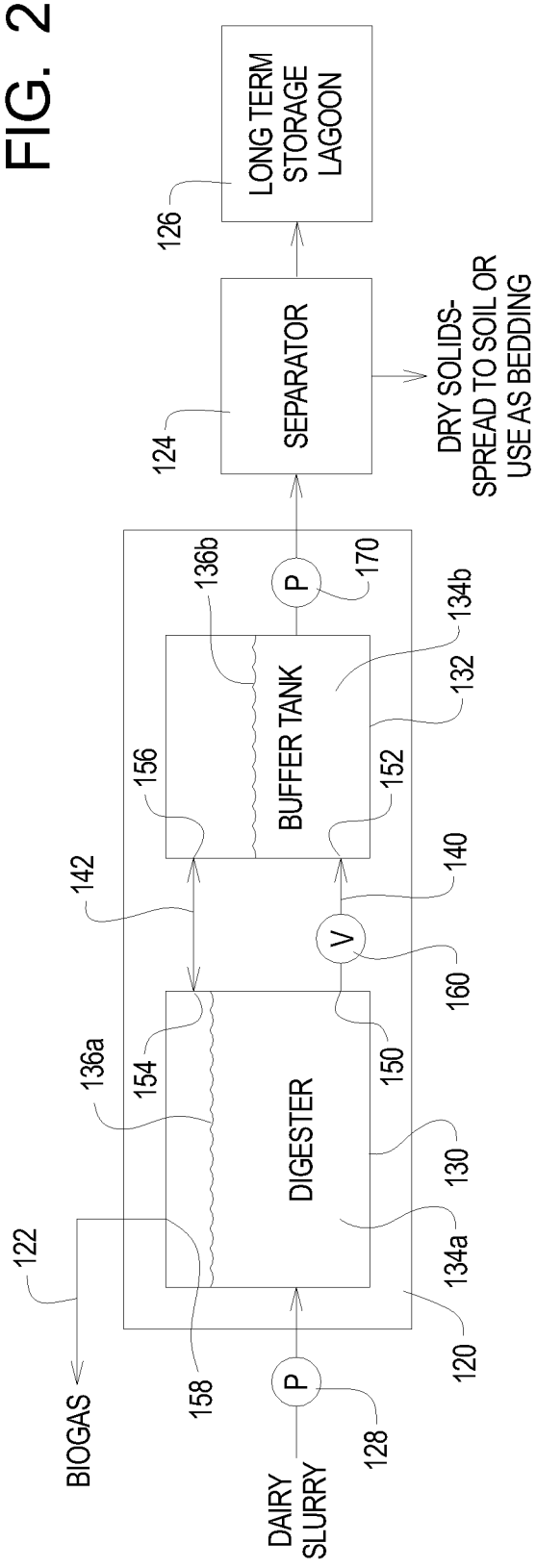
FIG. 2 is a schematic diagram of a second example anaerobic digester system of the present invention.

Referring now to FIG. 2 of the drawing, depicted therein is a second example anaerobic digester system 120. Biogas is removed from the second example digester system 120 through a biogas conduit 122. The second example anaerobic digester system 120 configured to be used with a separator 124 for separating separator feed material into dry solids and liquids. Liquids may be directed to a long term storage lagoon 126 or the like. FIG. 2 further illustrates that the second example anaerobic digester system 120 is also operatively connected to a feed pump 128 that feeds raw feed material into the digester system 120. The separator 124, long term storage lagoon 126, and feed pump 128 are or may be conventional and are described herein only to the extent necessary for a complete understanding of the present invention.

As shown in FIG. 2, the second example anaerobic digester system 120 comprises a primary digester tank 130 and a secondary or buffer digester tank 132. A primary feed material portion 134a being processed by the example digester system 120 is within the primary digester tank 130 as shown in FIG. 2. The primary feed material portion 134a within the primary digester tank 130 defines a primary feed material level 136a. FIG. 2 also illustrates that a secondary feed material portion 134b is within the secondary digester tank 132, and the secondary feed material portion 134b within the secondary digester tank 132 defines a secondary feed material level 136b.

First and second conduits 140 and 142 connect the primary digester tank 130 to the secondary digester tank 132. In particular, the first conduit 140 is configured to define a primary tank lower opening 150 and a secondary tank lower opening 152. The second conduit 142 is configured to define a digester tank upper opening 154 and a secondary tank upper opening 156. The first conduit 140 is arranged such that the primary tank lower opening 150 and secondary tank lower opening 152 are within the primary and secondary digester tanks 130 and 132 below the primary feed material level 136a and secondary feed material level 136b, respectively. The second conduit 142 is arranged such that the digester tank upper opening 154 and secondary tank upper opening 156 are within the primary and secondary digester tanks 130 and 132 above the primary feed material level 136a and secondary feed material level 136b, respectively. The biogas conduit 122 defines a biogas opening 158 through which biogas passes from the primary digester tank 130 into the biogas conduit 122, and the biogas opening 158 is also above the primary feed material level 136a. Further, for reasons that will be explained in further detail below, the primary tank lower opening 150 is arranged at or near a bottom of the interior of the primary digester tank 130.

FIG. 2 further illustrates that a flow control valve 160 is arranged to control flow of fluid through the first conduit 140. The flow control valve 160 operates in a closed configuration and at least one open configuration. Typically, the flow control valve 160 may operate in a continuum of open configurations between the closed configuration and a fully open configuration. In the closed configuration, the flow control valve 160 prevents flow of fluid through the first conduit 140. In any open configuration, the flow control valve 160 allows fluid flow between the primary digester tank 130 and the secondary digester tank 132 through the first conduit 140. A pump 170 is configured to force fluid from the secondary digester tank 132 to the separator 124.

The second example anaerobic digester system 120 operates generally as follows. The feed pump 128 pumps the primary feed material 134a into the primary digester tank 130. The primary digester tank 130 is operated in a conventional manner to generate biogas and digestate. The biogas is removed from the primary digester tank 130 through the biogas opening 158 and the biogas conduit 122.

The primary digester tank 130 is sized and dimensioned relative to the secondary digester tank 132 such that the head pressure within the primary digester tank 130 is much greater than the head pressure within the secondary digester tank 132. Periodically, a portion of the primary feed material 134a comprising the digestate, liquid material, and solid contaminate (such as sand) is allowed to flow at a first, relatively high, flow rate from the primary digester tank 130 into the secondary digester tank 132. In particular, a portion of the primary feed material 134a flows through the first conduit 140 and the flow control valve 160 and into the secondary digester tank 132 to form the secondary feed material 134b. The first conduit 140 and flow control valve 160 are sized, dimensioned, and/or controlled such that the head pressure within the primary digester tank 130 forces a portion of the secondary feed material 134a from the primary digester tank 130 to the secondary digester tank 132 at the first flow rate (e.g., 6000 gpm) for a short period of flush time.

The flush time duration depends on factors such as the relative sizes of the primary digester tank 130 and secondary digester tank 132, the size of the first conduit 140, and the nature of the feed material. The flush time duration should be sufficient to flush feed material having a relatively high concentration of solid contaminate from the primary digester tank 130. However, the flush time duration should be kept short enough such that primarily feed material with a relatively high concentration of solid contaminate is removed from the primary digester tank 130. The valve 160 is configured to be fully open for a flush time duration within a first range of approximately 10-15 seconds or a second range of approximately 5-20 seconds. Because they type of valve use as the example valve 160 (e.g., butterfly valve) may take from 3-5 seconds to open, the total time from initiation of the flush process to cessation of the flush process may be in a first range of 16-25 seconds or a second range of 11-30 seconds.

The primary tank lower opening 150 is arranged and the first flow rate selected such that the solid contaminate that has accumulated at the bottom of the primary digester tank 130 is flushed out of the primary digester tank 130 along with some of the digestate and liquid material. Accordingly, the secondary feed material 134b within the secondary digester tank 132 typically contains a much higher percentage of solid contaminate than the primary feed material 134a within the primary digester tank 130.

The anaerobic digestion process continues to act on the secondary feed material 134b in the secondary digester tank 132, and any biogas generated in the secondary digester tank 132 flows from the secondary digester tank 132 into the primary digester tank 130 through the second conduit 142. At the same time, the secondary feed material 134b may be periodically or continuously pumped by the pump 170 out of the secondary digester tank 132 and into the separator 124 at a second, relatively low, flow rate (e.g., 50 gpm). The separator 124 separates the secondary feed material 134b into dry solids and liquids. The digestate forms at least a part of the dry solids and may be removed from contaminate and used or otherwise safely disposed of.

Solid contaminate, especially non-digestible, relatively dense solids such as sand, will thus be carried by the intense, short duration flow of feed material from the primary digester tank 130 to the secondary digester tank 132. In particular, non-digestible solids that are more dense than the liquids (primarily water) forming the primary feed material 134a will sink to the bottom of the primary digester tank 130 such that such solid contaminates, and especially non-digestible, relatively dense solid contaminates such as sand, are relatively highly concentrated within the bottom of the primary digester tank 130. The primary feed material 134a flushed from the primary digester tank 130 and into the secondary digester tank 132 through the first conduit 140 and the flow control valve 160 will thus contain a higher concentration of solid contaminates than the primary feed material 134a that remains within the primary digester tank 130.

Accordingly, by periodically removing a relatively small amount of primary feed material 134a with a high concentration of solid contaminate, especially non-digestible, relatively dense solids such as sand, from the primary digester tank 130, the primary digester tank 130 is continually cleaned and thus allowed to operate at a relatively high level of efficiency in comparison to a digester system not having a secondary digester tank 132.

Characteristics of the second example anaerobic digester system 120 may be the same as those defined above with reference to the first example digester system 20.

III. Third Example Anaerobic Digester System

Figure 3:
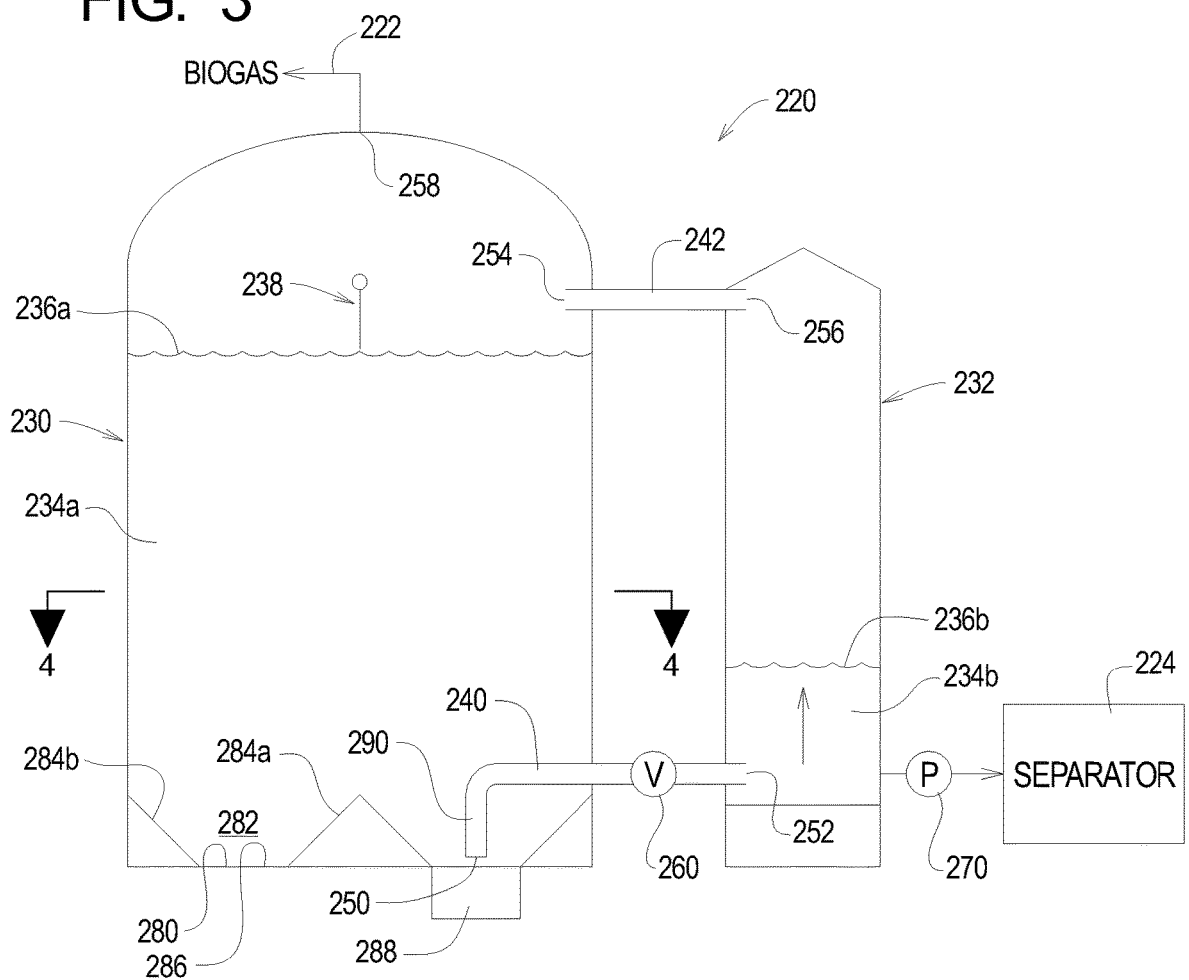
FIG. 3 is a somewhat schematic side elevation view of a digester tank and buffer tank of a third example anaerobic digester system the present invention.
Figure 4:
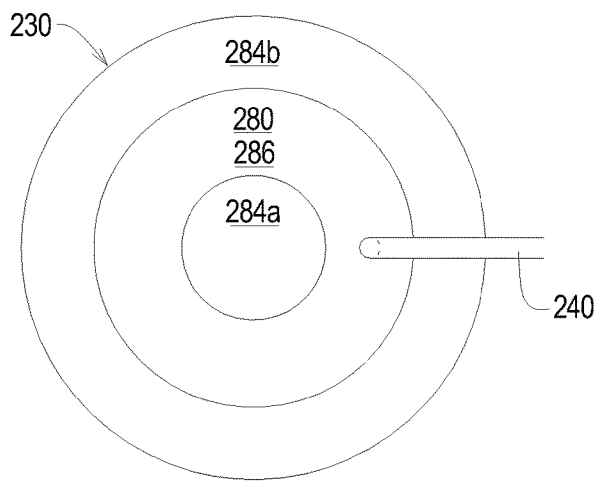
FIG. 4 is a top plan section view taken along lines 4-4 in FIG. 3.

Referring now to FIGS. 3 and 4 of the drawing, depicted therein is a third example anaerobic digester system 220. Biogas is removed from the second example digester system 220 through a biogas conduit 222. The third example anaerobic digester system 220 configured to be used with a separator 224 for separating separator feed material into dry solids and liquids. Liquids may be directed to a long term storage lagoon (not shown) or the like. The third example anaerobic digester system 220 may also be operatively connected to a feed pump (not shown) that feeds raw feed material into the digester system 220. The separator 224, long term storage lagoon, and feed pump are or may be conventional and are described herein only to the extent necessary for a complete understanding of the present invention.

As shown in FIG. 3, the third example anaerobic digester system 220 comprises a primary digester tank 230 and a secondary or buffer digester tank 232. A primary feed material portion 234a being processed by the example digester system 220 is within the primary digester tank 230 as shown in FIG. 3. The primary feed material portion 234a within the primary digester tank 230 defines a primary feed material level 236a. FIG. 3 also illustrates that a secondary feed material portion 234b is within the secondary digester tank 232, and the secondary feed material portion 234b within the secondary digester tank 232 defines a secondary feed material level 236b. A primary feed material sensor 238 is arranged within the primary digester tank 230 to determine a level of the primary feed material 234a within the primary digester tank 230.

First and second conduits 240 and 242 connect the primary digester tank 230 to the secondary digester tank 232. The first conduit 240 is configured to define a primary tank lower opening 250 and a secondary tank lower opening 252. The second conduit 242 is configured to define a digester tank upper opening 254 and a secondary tank upper opening 256. The first conduit 240 is arranged such that the primary tank lower opening 250 and secondary tank lower opening 252 are within the primary and secondary digester tanks 230 and 232 below the primary feed material level 236a and secondary feed material level 236b, respectively. The second conduit 240 is arranged such that the digester tank upper opening 254 and secondary tank upper opening 256 are within the primary and secondary digester tanks 230 and 232 above the primary feed material level 236a and secondary feed material level 236b, respectively. The biogas conduit 222 defines a biogas opening 258 through which biogas passes from the primary digester tank 230 into the biogas conduit 222, and the biogas opening 258 is also above the primary feed material level 236a. Further, for reasons that will be explained in further detail below, the primary tank lower opening 250 is arranged at or near a bottom of the interior of the primary tank 230.

FIG. 3 further illustrates that a flow control valve 260 is arranged to control flow of fluid through the first conduit 240. The flow control valve 260 operates in a closed configuration and at least one open configuration. Typically, the flow control valve 260 may operate in a continuum of open configurations between the closed configuration and a fully open configuration. In the closed configuration, the flow control valve 260 prevents flow of fluid through the first conduit 240. In any open configuration, the flow control valve 260 allows fluid flow between the primary digester tank 230 and the secondary digester tank 232 through the first conduit 240. A pump 270 is configured to force fluid from the secondary digester tank 232 to the separator 224.

FIGS. 3 and 4 illustrate that a bottom wall 280 of the example primary digester tank 230 defines a trough region 282. In particular, the bottom wall 280 comprises inner and outer side walls 284a and 284b and an intermediate wall 286 connecting the inner and outer side walls 284a and 284b. Optionally, a sump 288 may be arranged along at least a portion of the intermediate wall 286 to facilitate draining of the primary digester tank 230.

FIGS. 3 and 4 further illustrate that the example intermediate wall 286 defines a flat, annular shape and is substantially horizontal during normal operation of the third example anaerobic digester system 220. The inner side wall 284a takes the form of an inverted frustoconical shape, while the outer side wall 284b takes the form a frustoconical shape of greater diameter than the shape defined by the inner side wall 284a. Solid contaminate, and in particular relatively dense solid contaminate such as sand, that settles to the bottom of the primary digester tank 230 will be directed inwardly by the side walls 284a and 284b and onto the intermediate wall 286, thus further concentrating the solid contaminate at the bottom of the primary digester tank.

FIG. 3 further illustrates that the example first conduit 240 defines a downwardly extending portion 290 that is configured such that the primary tank lower opening 250 is arranged immediately above and directed towards a portion of the intermediate wall 286 and is also arranged between portions of the inner and outer side walls 284a and 284b. The downwardly extending portion 290 of the example first conduit 240 is sized, dimensioned, and arranged to optimize the flow of primary feed material 234a with a higher concentration of solid contaminates out of the primary digester tank 230 when the flow control valve 260 is in its open configuration.

The third example anaerobic digester system 220 operates generally as follows. The feed pump continuously or periodically pumps the primary feed material 234a into the primary digester tank 230. The primary digester tank 230 is operated in a conventional manner to generate biogas and digestate. The biogas is removed from the primary digester tank 230 through the biogas opening and the biogas conduit.

When the primary feed material level sensor 238 determines that the primary feed material level 236a reaches a predetermined value, the flow control valve 260 is placed in an open configuration. The head pressure within the primary digester tank 230 is much greater than the head pressure within the secondary digester tank 232. Accordingly, when the flow control valve 260 is open, a portion of the primary feed material 234a comprising the digestate, liquid material, and solid contaminate (such as sand) flows at a first, relatively high, flow rate from the primary digester tank 230 into the secondary digester tank 232. In particular, a portion of the primary feed material 234a flows through the first conduit 240 and the flow control valve 260 and into the secondary digester tank 232 to form the secondary feed material 234b. The first conduit 240 and flow control valve 260 are sized, dimensioned, and/or controlled such that the head pressure within the primary digester tank 230 forces a portion of the primary feed material 234a from the primary digester tank 230 to the secondary digester tank 232 at the first flow rate (e.g., 6000 gpm) for a short period of time.

The location of the primary tank lower opening 250 is arranged and the first flow rate selected such that the solid contaminate that has accumulated at the bottom of the primary digester tank 230 is flushed out of the primary digester tank 230 along with the digestate and liquid material. Accordingly, the secondary feed material 234b within the secondary digester tank 232 typically contains a much higher percentage of solid contaminate than the primary feed material 234a within the primary digester tank 230.

The anaerobic digestion process continues to act on the secondary feed material 234b in the secondary digester tank 232, and any biogas generated in the secondary digester tank 232 flows from the secondary digester tank 232 into the primary digester tank 230 through the second conduit 242. At the same time, the secondary feed material 234b may be periodically or continuously pumped by the pump 270 out of the secondary digester tank 232 and into the separator 222 at a second, relatively low, flow rate (e.g., 50 gpm). The separator 222 separates the secondary feed material 234b into dry solids and liquids. The digestate forms at least a part of the dry solids and may be removed from contaminate and used or otherwise safely disposed of.

Solid contaminate, especially non-digestible, relatively dense solids such as sand, will thus be carried by the intense, short duration flow of feed material from the primary digester tank 230 to the secondary digester tank 232. In particular, non-digestible solids that are more dense than the liquids (primarily water) forming the primary feed material 234a will sink to the bottom of the primary digester tank 230 such that such solid contaminates, and especially non-digestible, relatively dense solid contaminates such as sand, are relatively highly concentrated within the bottom of the primary digester tank 230. The primary feed material 234a flushed from the primary digester tank 230 and into the secondary digester tank 232 through the first conduit 240 and the flow control valve 260 will thus contain a higher concentration of solid contaminates than the primary feed material 234a that remains within the primary digester tank 230.

Accordingly, by periodically removing a small amount of primary feed material 234a with a high concentration of solid contaminate, especially non-digestible, relatively dense solids such as sand, from the primary digester tank 230, the primary digester tank 230 is continually cleaned and thus allowed to operate at a relatively high level of efficiency in comparison to a digester system not having a secondary digester tank 232.

Characteristics of the third example anaerobic digester system 220 may be the same as those defined above with reference to the first example digester system 20.

IV. Fourth Example Anaerobic Digester System

Figure 5:
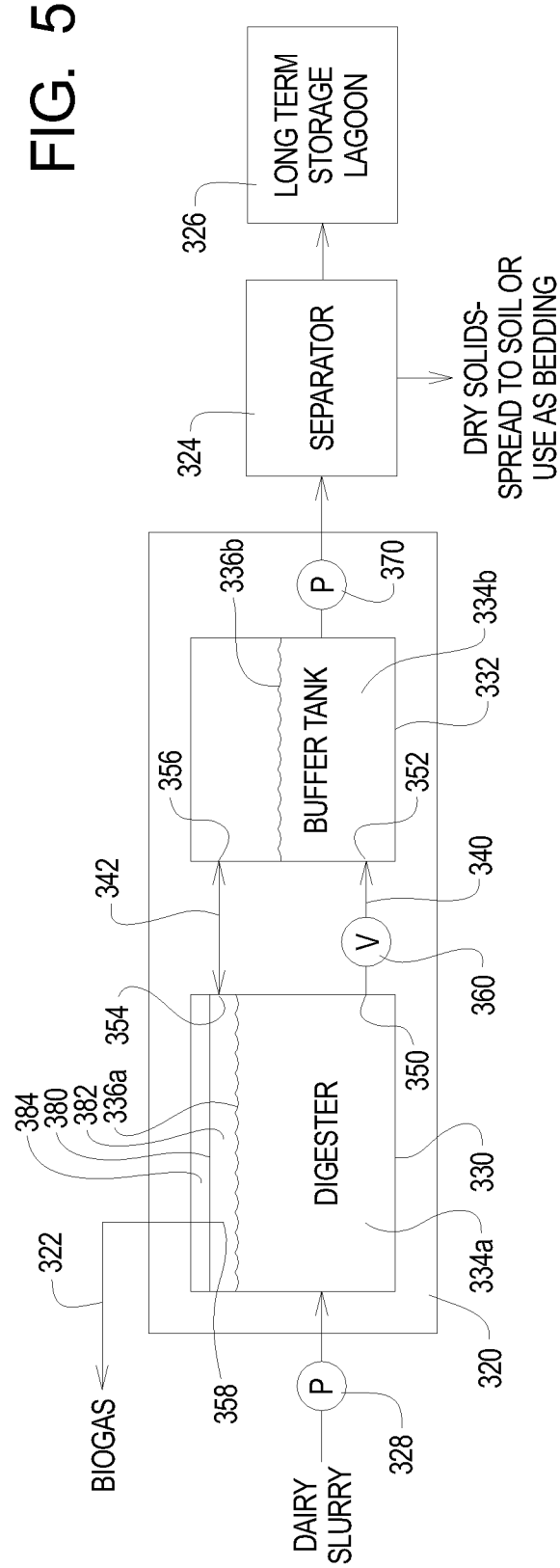
FIG. 5 is a schematic diagram of a fourth example anaerobic digester system of the present invention.

Referring now to FIG. 5 of the drawing, depicted therein is a fourth example anaerobic digester system 320. Biogas is removed from the fourth example digester system 320 through a biogas conduit 322. The fourth example anaerobic digester system 320 configured to be used with a separator 324 for separating separator feed material into dry solids and liquids. Liquids may be directed to a long term storage lagoon 326 or the like. FIG. 5 further illustrates that the fourth example anaerobic digester system 320 is also operatively connected to a feed pump 328 that feeds raw feed material into the digester system 320. The separator 324, long term storage lagoon 326, and feed pump 328 are or may be conventional and are described herein only to the extent necessary for a complete understanding of the present invention.

As shown in FIG. 5, the fourth example anaerobic digester system 320 comprises a primary digester tank 330 and a secondary or buffer digester tank 332. A primary feed material portion 334a being processed by the example digester system 320 is within the primary digester tank 330 as shown in FIG. 5. The primary feed material portion 334a within the primary digester tank 330 defines a primary feed material level 336a. FIG. 5 also illustrates that a secondary feed material portion 334b is within the secondary digester tank 332, and the secondary feed material portion 334b within the secondary digester tank 332 defines a secondary feed material level 336b.

First and second conduits 340 and 342 connect the primary digester tank 330 to the secondary digester tank 332. In particular, the first conduit 340 is configured to define a primary tank lower opening 350 and a secondary tank lower opening 352. The second conduit 342 is configured to define a digester tank upper opening 354 and a secondary tank upper opening 356. The first conduit 340 is arranged such that the primary tank lower opening 350 and secondary tank lower opening 352 are within the primary and secondary digester tanks 330 and 332 below the primary feed material level 336a and secondary feed material level 336b, respectively. The second conduit 342 is arranged such that the digester tank upper opening 354 and secondary tank upper opening 356 are within the primary and secondary digester tanks 330 and 332 above the primary feed material level 336a and secondary feed material level 336b, respectively. The biogas conduit 322 defines a biogas opening 358 through which biogas passes from the primary digester tank 330 into the biogas conduit 322, and the biogas opening 358 is also above the primary feed material level 336a. Further, for reasons that will be explained in further detail below, the primary tank lower opening 350 is arranged at or near a bottom of the interior of the primary digester tank 332.

FIG. 5 further illustrates that a flow control valve 360 is arranged to control flow of fluid through the first conduit 340. The flow control valve 360 operates in a closed configuration and at least one open configuration. Typically, the flow control valve 360 may operate in a continuum of open configurations between the closed configuration and a fully open configuration. In the closed configuration, the flow control valve 360 prevents flow of fluid through the first conduit 340. In any open configuration, the flow control valve 360 allows fluid flow between the primary digester tank 330 and the secondary digester tank 332 through the first conduit 340. A pump 370 is configured to force fluid from the secondary digester tank 332 to the separator 324.

A membrane 380 is arranged within the example primary digester tank 330. The example membrane 380 separates the region of the primary digester tank 330 above the primary feed material level 336a into first and second regions 382 and 384. Biogas created by the digestion process collects in the first region 382, and the biogas opening 358 is in fluid communication with the first region 382. The example membrane 380 is flexible and fluid tight. In the fourth example anaerobic digester system 320, the digester tank upper opening 354 is also in fluid communication with the first region 382.

The fourth example anaerobic digester system 320 operates generally as follows. The feed pump 328 pumps the primary feed material 334a into the primary digester tank 330. The primary digester tank 330 is operated in a conventional manner to generate biogas and digestate. Biogas will collect or accumulate within first region 382 and deform the example membrane 380. The biogas is removed from the first region 382 of the primary digester tank 330 through the biogas opening 358 and the biogas conduit 322.

The primary digester tank 330 is sized and dimensioned relative to the secondary digester tank 332 such that the head pressure within the primary digester tank 330 is much greater than the head pressure within the secondary digester tank 332. Periodically, a portion of the primary feed material 334a comprising the digestate, liquid material, and solid contaminate (such as sand) is allowed to flow at a first, relatively high, flow rate from the primary digester tank 330 into the secondary digester tank 332. In particular, a portion of the primary feed material 334a flows through the first conduit 340 and the flow control valve 360 and into the secondary digester tank 332 to form the secondary feed material 334b. The first conduit 340 and flow control valve 360 are sized, dimensioned, and/or controlled such that the head pressure within the primary digester tank 330 forces a portion of the secondary feed material 334a from the primary digester tank 330 to the secondary digester tank 332 at the first flow rate (e.g., 6000 gpm) for a short period of flush time.

The flush time duration depends on factors such as the relative sizes of the primary digester tank 330 and secondary digester tank 332, the size of the first conduit 340, and the nature of the feed material. The flush time duration should be sufficient to flush feed material having a relatively high concentration of solid contaminate from the primary digester tank 330. However, the flush time duration should be kept short enough such that primarily feed material with a relatively high concentration of solid contaminate is removed from the primary digester tank 330. The valve 360 is configured to be fully open for a flush time duration within a first range of approximately 30-15 seconds or a second range of approximately 5-20 seconds. Because they type of valve use as the example valve 360 (e.g., butterfly valve) may take from 3-5 seconds to open, the total time from initiation of the flush process to cessation of the flush process may be in a first range of 36-25 seconds or a second range of 31-30 seconds.

The primary tank lower opening 350 is arranged and the first flow rate selected such that the solid contaminate that has accumulated at the bottom of the primary digester tank 330 is flushed out of the primary digester tank 330 along with some of the digestate and liquid material. Accordingly, the secondary feed material 334b within the secondary digester tank 332 typically contains a much higher percentage of solid contaminate than the primary feed material 334a within the primary digester tank 330.

The anaerobic digestion process continues to act on the secondary feed material 334b in the secondary digester tank 332, and any biogas generated in the secondary digester tank 332 flows from the secondary digester tank 332 into the primary digester tank 330 through the second conduit 342. At the same time, the secondary feed material 334b may be periodically or continuously pumped by the pump 370 out of the secondary digester tank 332 and into the separator 324 at a second, relatively low, flow rate (e.g., 50 gpm). The separator 324 separates the secondary feed material 334b into dry solids and liquids. The digestate forms at least a part of the dry solids and may be removed from contaminate and used or otherwise safely disposed of.

Solid contaminate, especially non-digestible, relatively dense solids such as sand, will thus be carried by the intense, short duration flow of feed material from the primary digester tank 330 to the secondary digester tank 332. In particular, non-digestible solids that are more dense than the liquids (primarily water) forming the primary feed material 334a will sink to the bottom of the primary digester tank 330 such that such solid contaminates, and especially non-digestible, relatively dense solid contaminates such as sand, are relatively highly concentrated within the bottom of the primary digester tank 330. The primary feed material 334a flushed from the primary digester tank 330 and into the secondary digester tank 332 through the first conduit 340 and the flow control valve 360 will thus contain a higher concentration of solid contaminates than the primary feed material 334a that remains within the primary digester tank 330.

Accordingly, by periodically removing a relatively small amount of primary feed material 334a with a high concentration of solid contaminate, especially non-digestible, relatively dense solids such as sand, from the primary digester tank 330, the primary digester tank 330 is continually cleaned and thus allowed to operate at a relatively high level of efficiency in comparison to a digester system not having a secondary digester tank 332.

Characteristics of the fourth example anaerobic digester system 320 may be the same as those defined above with reference to the first example digester system 20.

V. Fifth Example Anaerobic Digester System

Figure 6:
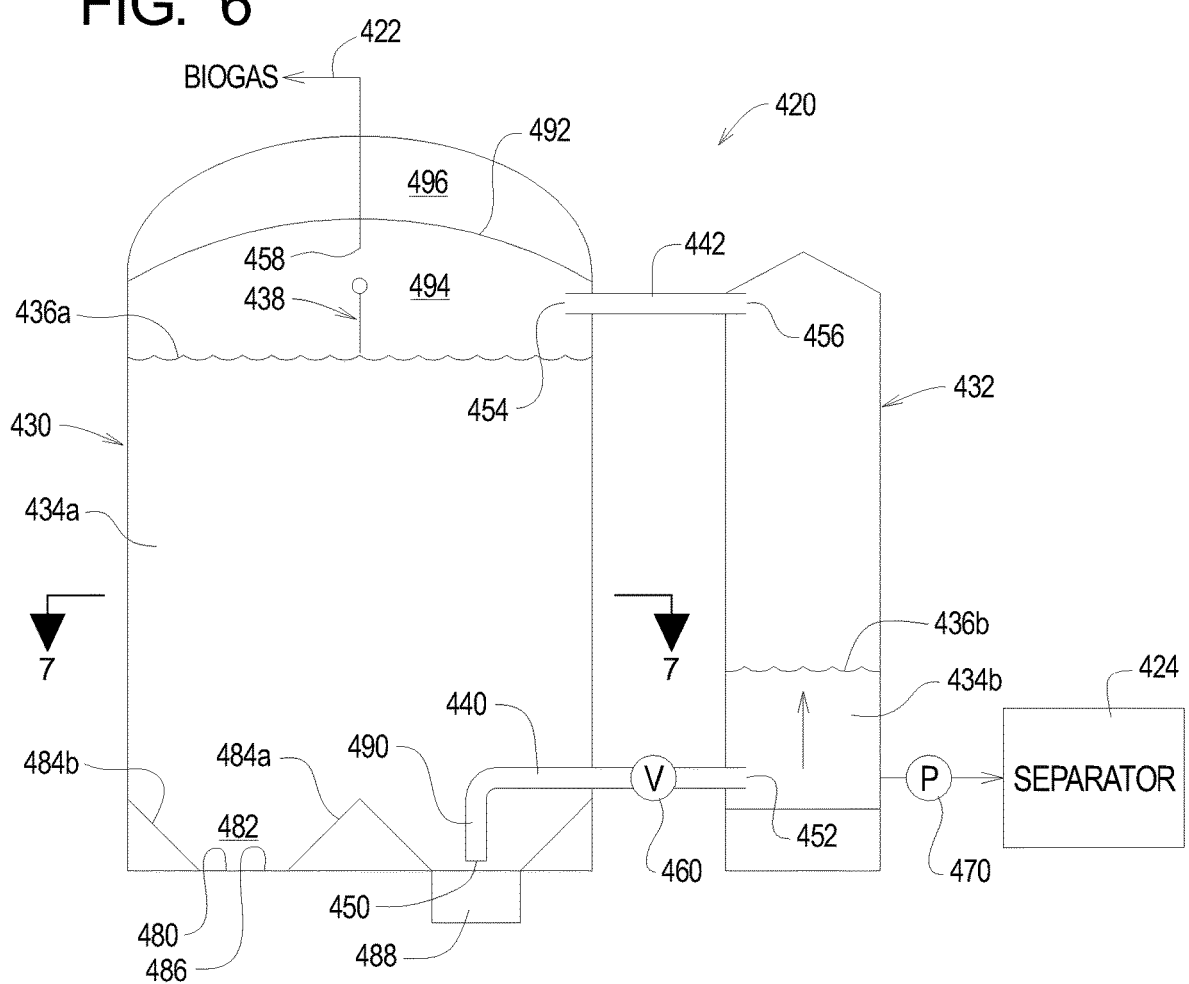
FIG. 6 is a somewhat schematic side elevation view of a digester tank and buffer tank of a fifth example anaerobic digester system the present invention.
Figure 7:
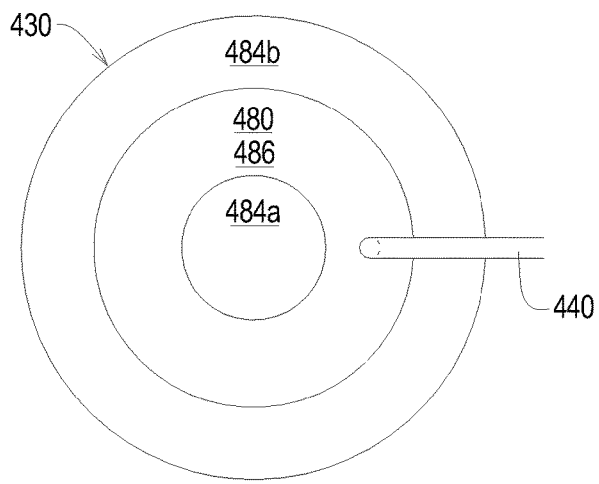
FIG. 7 is a top plan section view taken along lines 7-7 in FIG. 6.

Referring now to FIGS. 6 and 7 of the drawing, depicted therein is a fifth example anaerobic digester system 420. Biogas is removed from the second example digester system 420 through a biogas conduit 422. The fifth example anaerobic digester system 420 configured to be used with a separator 424 for separating separator feed material into dry solids and liquids. Liquids may be directed to a long term storage lagoon (not shown) or the like. The fifth example anaerobic digester system 420 may also be operatively connected to a feed pump (not shown) that feeds raw feed material into the digester system 420. The separator 424, long term storage lagoon, and feed pump are or may be conventional and are described herein only to the extent necessary for a complete understanding of the present invention.

As shown in FIG. 6, the fifth example anaerobic digester system 420 comprises a primary digester tank 430 and a secondary or buffer digester tank 432. A primary feed material portion 434a being processed by the example digester system 420 is within the primary digester tank 430 as shown in FIG. 6. The primary feed material portion 434a within the primary digester tank 430 defines a primary feed material level 436a. FIG. 6 also illustrates that a secondary feed material portion 434b is within the secondary digester tank 432, and the secondary feed material portion 434b within the secondary digester tank 432 defines a secondary feed material level 436b. A primary feed material level sensor 438 is arranged within the primary digester tank 430 to determine a level of the primary feed material 434a within the primary digester tank 430.

First and second conduits 440 and 442 connect the primary digester tank 430 to the secondary digester tank 432. The first conduit 440 is configured to define a primary tank lower opening 450 and a secondary tank lower opening 452. The second conduit 442 is configured to define a digester tank upper opening 454 and a secondary tank upper opening 456. The first conduit 440 is arranged such that the primary tank lower opening 450 and secondary tank lower opening 452 are within the primary and secondary digester tanks 430 and 432 below the primary feed material level 436a and secondary feed material level 436b, respectively. The second conduit 442 is arranged such that the digester tank upper opening 454 and secondary tank upper opening 456 are within the primary and secondary digester tanks 430 and 432 above the primary feed material level 436a and secondary feed material level 436b, respectively. The biogas conduit 422 defines a biogas opening 458 through which biogas passes from the primary digester tank 430 into the biogas conduit 422, and the biogas opening 458 is also above the primary feed material level 436a. Further, for reasons that will be explained in further detail below, the primary tank lower opening 450 is arranged at or near a bottom of the interior of the primary tank 430.

FIG. 6 further illustrates that a flow control valve 460 is arranged to control flow of fluid through the first conduit 440. The flow control valve 460 operates in a closed configuration and at least one open configuration. Typically, the flow control valve 460 may operate in a continuum of open configurations between the closed configuration and a fully open configuration. In the closed configuration, the flow control valve 460 prevents flow of fluid through the first conduit 440. In any open configuration, the flow control valve 460 allows fluid flow between the primary digester tank 430 and the secondary digester tank 432 through the first conduit 440. A pump 470 is configured to force fluid from the secondary digester tank 432 to the separator 424.

FIGS. 6 and 7 illustrate that a bottom wall 480 of the example primary digester tank 430 defines a trough region 482. In particular, the bottom wall 480 comprises inner and outer side walls 484a and 484b and an intermediate wall 486 connecting the inner and outer side walls 484a and 484b. Optionally, a sump 488 may be arranged along at least a portion of the intermediate wall 486 to facilitate draining of the primary digester tank 430.

FIGS. 6 and 7 further illustrate that the example intermediate wall 486 defines a flat, annular shape and is substantially horizontal during normal operation of the fifth example anaerobic digester system 420. The inner side wall 484a takes the form of an inverted frustoconical shape, while the outer side wall 484b takes the form a frustoconical shape of greater diameter than the shape defined by the inner side wall 484a. Solid contaminate, and in particular relatively dense solid contaminate such as sand, that settles to the bottom of the primary digester tank 430 will be directed inwardly by the side walls 484a and 484b and onto the intermediate wall 486, thus further concentrating the solid contaminate at the bottom of the primary digester tank.

FIG. 6 further illustrates that the example first conduit 440 defines a downwardly extending portion 490 that is configured such that the primary tank lower opening 450 is arranged immediately above and directed towards a portion of the intermediate wall 486 and is also arranged between portions of the inner and outer side walls 484a and 484b. The downwardly extending portion 490 of the example first conduit 440 is sized, dimensioned, and arranged to optimize the flow of primary feed material 434a with a higher concentration of solid contaminates out of the primary digester tank 430 when the flow control valve 460 is in its open configuration.

A membrane 492 is arranged within the example primary digester tank 430. The example membrane 492 separates the region of the primary digester tank 430 above the primary feed material level 436a into first and second regions 494 and 496. Biogas created by the digestion process collects in the first region 482, and the biogas opening 458 is in fluid communication with the first region 482. The example membrane 480 is flexible and fluid tight. In the fourth example anaerobic digester system 420, the digester tank upper opening 454 is also in fluid communication with the first region 482.

The fifth example anaerobic digester system 420 operates generally as follows. The feed pump continuously or periodically pumps the primary feed material 434a into the primary digester tank 430. The primary digester tank 430 is operated in a conventional manner to generate biogas and digestate. Biogas will collect or accumulate within first region 482 and deform the example membrane 492. The biogas is removed from the primary digester tank 430 through the biogas opening and the biogas conduit.

When the primary feed material level sensor 438 determines that the primary feed material level 436a reaches a predetermined value, the flow control valve 460 is placed in an open configuration. The head pressure within the primary digester tank 430 is much greater than the head pressure within the secondary digester tank 432. Accordingly, when the flow control valve 460 is open, a portion of the primary feed material 434a comprising the digestate, liquid material, and solid contaminate (such as sand) flows at a first, relatively high, flow rate from the primary digester tank 430 into the secondary digester tank 432. In particular, a portion of the primary feed material 434a flows through the first conduit 440 and the flow control valve 460 and into the secondary digester tank 432 to form the secondary feed material 434b. The first conduit 440 and flow control valve 460 are sized, dimensioned, and/or controlled such that the head pressure within the primary digester tank 430 forces a portion of the primary feed material 434a from the primary digester tank 430 to the secondary digester tank 432 at the first flow rate (e.g., 6000 gpm) for a short period of time.

The location of the primary tank lower opening 450 is arranged and the first flow rate selected such that the solid contaminate that has accumulated at the bottom of the primary digester tank 430 is flushed out of the primary digester tank 430 along with the digestate and liquid material. Accordingly, the secondary feed material 434b within the secondary digester tank 432 typically contains a much higher percentage of solid contaminate than the primary feed material 434a within the primary digester tank 430.

The anaerobic digestion process continues to act on the secondary feed material 434b in the secondary digester tank 432, and any biogas generated in the secondary digester tank 432 flows from the secondary digester tank 432 into the primary digester tank 430 through the second conduit 442. At the same time, the secondary feed material 434b may be periodically or continuously pumped by the pump 470 out of the secondary digester tank 432 and into the separator 424 at a second, relatively low, flow rate (e.g., 50 gpm). The separator 424 separates the secondary feed material 434b into dry solids and liquids. The digestate forms at least a part of the dry solids and may be removed from contaminate and used or otherwise safely disposed of.

Solid contaminate, especially non-digestible, relatively dense solids such as sand, will thus be carried by the intense, short duration flow of feed material from the primary digester tank 430 to the secondary digester tank 432. In particular, non-digestible solids that are more dense than the liquids (primarily water) forming the primary feed material 434a will sink to the bottom of the primary digester tank 430 such that such solid contaminates, and especially non-digestible, relatively dense solid contaminates such as sand, are relatively highly concentrated within the bottom of the primary digester tank 430. The primary feed material 434a flushed from the primary digester tank 430 and into the secondary digester tank 432 through the first conduit 440 and the flow control valve 460 will thus contain a higher concentration of solid contaminates than the primary feed material 434a that remains within the primary digester tank 430.

Accordingly, by periodically removing a small amount of primary feed material 434a with a high concentration of solid contaminate, especially non-digestible, relatively dense solids such as sand, from the primary digester tank 430, the primary digester tank 430 is continually cleaned and thus allowed to operate at a relatively high level of efficiency in comparison to a digester system not having a secondary digester tank 432.

Characteristics of the fifth example anaerobic digester system 420 may be the same as those defined above with reference to the first example digester system 20.

VI. Sixth Example Anaerobic Digester System

Figure 8:
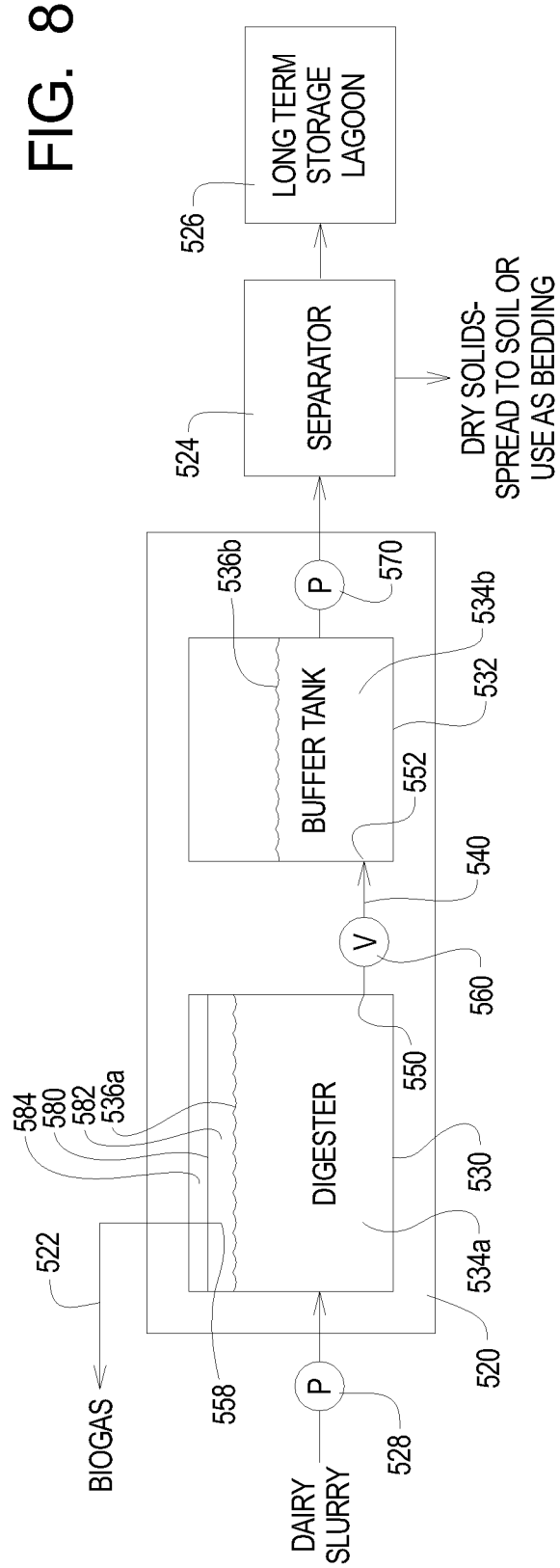
FIG. 8 is a schematic diagram of a sixth example anaerobic digester system of the present invention.

Referring now to FIG. 8 of the drawing, depicted therein is a sixth example anaerobic digester system 520. Biogas is removed from the sixth example digester system 520 through a biogas conduit 522. The sixth example anaerobic digester system 520 configured to be used with a separator 524 for separating separator feed material into dry solids and liquids. Liquids may be directed to a long term storage lagoon 526 or the like. FIG. 8 further illustrates that the sixth example anaerobic digester system 520 is also operatively connected to a feed pump 528 that feeds raw feed material into the digester system 520. The separator 524, long term storage lagoon 526, and feed pump 528 are or may be conventional and are described herein only to the extent necessary for a complete understanding of the present invention.

As shown in FIG. 8, the sixth example anaerobic digester system 520 comprises a primary digester tank 530 and a secondary or buffer digester tank 532. A primary feed material portion 534a being processed by the example digester system 520 is within the primary digester tank 530 as shown in FIG. 8. The primary feed material portion 534a within the primary digester tank 530 defines a primary feed material level 536a. FIG. 8 also illustrates that a secondary feed material portion 534b is within the secondary digester tank 532, and the secondary feed material portion 534b within the secondary digester tank 532 defines a secondary feed material level 536b.

A first conduit 540 connects the primary digester tank 530 to the secondary digester tank 532. In particular, the first conduit 540 is configured to define a primary tank lower opening 550 and a secondary tank lower opening 552. The first conduit 540 is arranged such that the primary tank lower opening 550 and secondary tank lower opening 552 are within the primary and secondary digester tanks 530 and 532 below the primary feed material level 536a and secondary feed material level 536b, respectively. The biogas conduit 522 defines a biogas opening 558 through which biogas passes from the primary digester tank 530 into the biogas conduit 522, and the biogas opening 558 is also above the primary feed material level 536a. Further, for reasons that will be explained in further detail below, the primary tank lower opening 550 is arranged at or near a bottom of the interior of the primary digester tank 532.

FIG. 8 further illustrates that a flow control valve 560 is arranged to control flow of fluid through the first conduit 540. The flow control valve 560 operates in a closed configuration and at least one open configuration. Typically, the flow control valve 560 may operate in a continuum of open configurations between the closed configuration and a fully open configuration. In the closed configuration, the flow control valve 560 prevents flow of fluid through the first conduit 540. In any open configuration, the flow control valve 560 allows fluid flow between the primary digester tank 530 and the secondary digester tank 532 through the first conduit 540. A pump 570 is configured to force fluid from the secondary digester tank 532 to the separator 524.

A membrane 580 is arranged within the example primary digester tank 530. The example membrane 580 separates the region of the primary digester tank 530 above the primary feed material level 536a into first and second regions 582 and 584. Biogas created by the digestion process collects in the first region 582, and the biogas opening 558 is in fluid communication with the first region 582. The example membrane 580 is flexible and fluid tight.

The sixth example anaerobic digester system 520 operates generally as follows. The feed pump 528 pumps the primary feed material 534a into the primary digester tank 530. The primary digester tank 530 is operated in a conventional manner to generate biogas and digestate. Biogas will collect or accumulate within first region 582 and deform the example membrane 580. The biogas is removed from the first region 582 of the primary digester tank 530 through the biogas opening 558 and the biogas conduit 522.

The primary digester tank 530 is sized and dimensioned relative to the secondary digester tank 532 such that the head pressure within the primary digester tank 530 is much greater than the head pressure within the secondary digester tank 532. Periodically, a portion of the primary feed material 534a comprising the digestate, liquid material, and solid contaminate (such as sand) is allowed to flow at a first, relatively high, flow rate from the primary digester tank 530 into the secondary digester tank 532. In particular, a portion of the primary feed material 534a flows through the first conduit 540 and the flow control valve 560 and into the secondary digester tank 532 to form the secondary feed material 534b. The first conduit 540 and flow control valve 560 are sized, dimensioned, and/or controlled such that the head pressure within the primary digester tank 530 forces a portion of the secondary feed material 534a from the primary digester tank 530 to the secondary digester tank 532 at the first flow rate (e.g., 6000 gpm) for a short period of flush time.

The flush time duration depends on factors such as the relative sizes of the primary digester tank 530 and secondary digester tank 532, the size of the first conduit 540, and the nature of the feed material. The flush time duration should be sufficient to flush feed material having a relatively high concentration of solid contaminate from the primary digester tank 530. However, the flush time duration should be kept short enough such that primarily feed material with a relatively high concentration of solid contaminate is removed from the primary digester tank 530. The valve 560 is configured to be fully open for a flush time duration within a first range of approximately 50-15 seconds or a second range of approximately 5-20 seconds. Because they type of valve use as the example valve 560 (e.g., butterfly valve) may take from 5-5 seconds to open, the total time from initiation of the flush process to cessation of the flush process may be in a first range of 56-25 seconds or a second range of 51-30 seconds.

The primary tank lower opening 550 is arranged and the first flow rate selected such that the solid contaminate that has accumulated at the bottom of the primary digester tank 530 is flushed out of the primary digester tank 530 along with some of the digestate and liquid material. Accordingly, the secondary feed material 534b within the secondary digester tank 532 typically contains a much higher percentage of solid contaminate than the primary feed material 534a within the primary digester tank 530.

The anaerobic digestion process continues to act on the secondary feed material 534b in the secondary digester tank 532. At the same time, the secondary feed material 534b may be periodically or continuously pumped by the pump 570 out of the secondary digester tank 532 and into the separator 524 at a second, relatively low, flow rate (e.g., 50 gpm). The separator 524 separates the secondary feed material 534b into dry solids and liquids. The digestate forms at least a part of the dry solids and may be removed from contaminate and used or otherwise safely disposed of.

Solid contaminate, especially non-digestible, relatively dense solids such as sand, will thus be carried by the intense, short duration flow of feed material from the primary digester tank 530 to the secondary digester tank 532. In particular, non-digestible solids that are more dense than the liquids (primarily water) forming the primary feed material 534a will sink to the bottom of the primary digester tank 530 such that such solid contaminates, and especially non-digestible, relatively dense solid contaminates such as sand, are relatively highly concentrated within the bottom of the primary digester tank 530. The primary feed material 534a flushed from the primary digester tank 530 and into the secondary digester tank 532 through the first conduit 540 and the flow control valve 560 will thus contain a higher concentration of solid contaminates than the primary feed material 534a that remains within the primary digester tank 530.

Accordingly, by periodically removing a relatively small amount of primary feed material 534a with a high concentration of solid contaminate, especially non-digestible, relatively dense solids such as sand, from the primary digester tank 530, the primary digester tank 530 is continually cleaned and thus allowed to operate at a relatively high level of efficiency in comparison to a digester system not having a secondary digester tank 532.

Characteristics of the sixth example anaerobic digester system 520 may be the same as those defined above with reference to the first example digester system 20.

VII. Seventh Example Anaerobic Digester System

Figure 9:
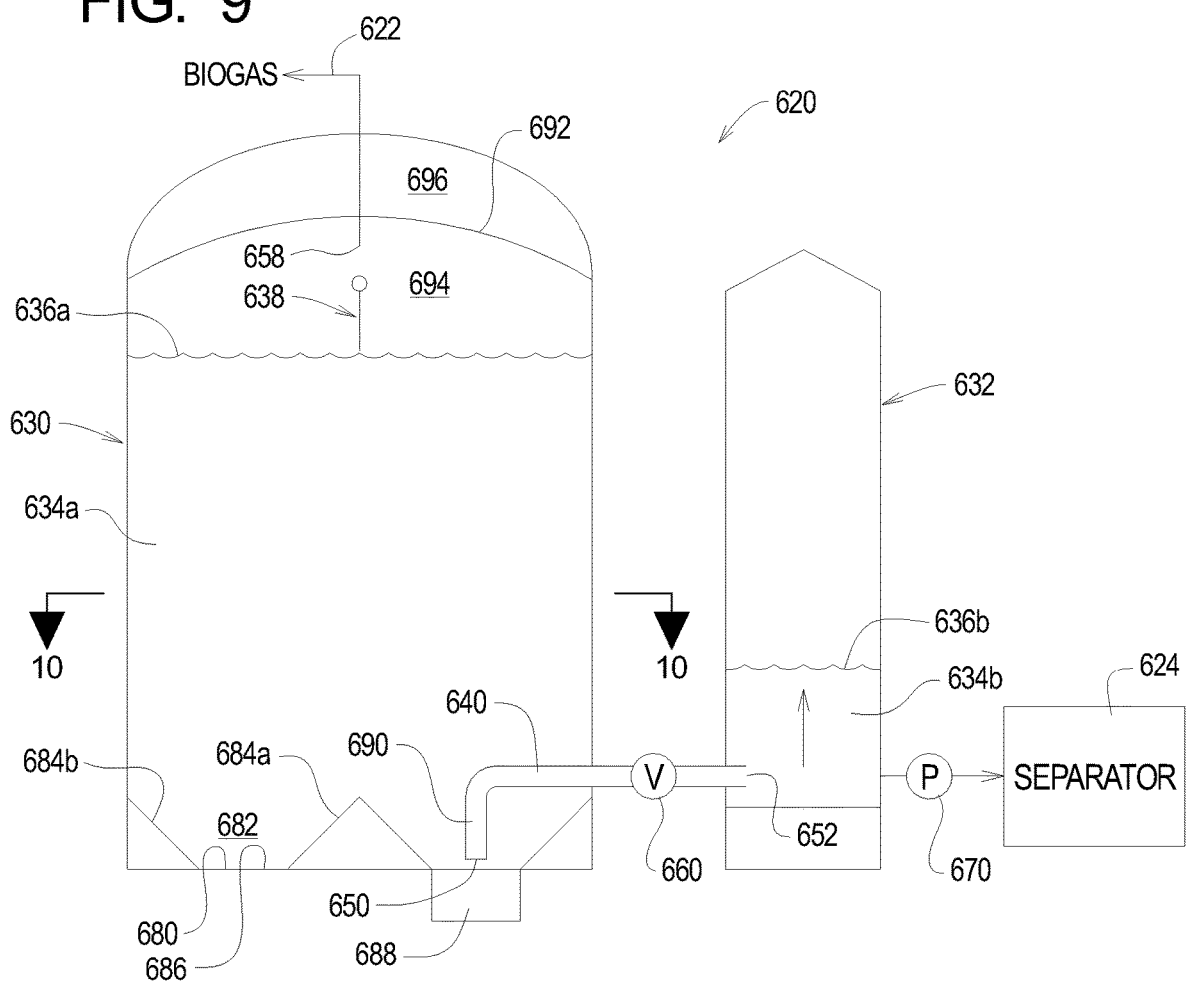
FIG. 9 is a somewhat schematic side elevation view of a digester tank and buffer tank of a seventh example anaerobic digester system the present invention.
Figure 10:
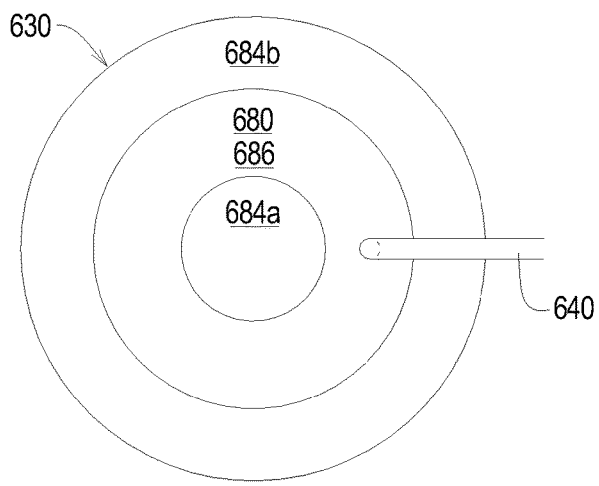
FIG. 10 is a top plan section view taken along lines 9-9 in FIG. 9.

Referring now to FIGS. 9 and 10 of the drawing, depicted therein is a seventh example anaerobic digester system 620. Biogas is removed from the seventh example digester system 620 through a biogas conduit 622. The seventh example anaerobic digester system 620 configured to be used with a separator 624 for separating separator feed material into dry solids and liquids. Liquids may be directed to a long term storage lagoon (not shown) or the like. The seventh example anaerobic digester system 620 may also be operatively connected to a feed pump (not shown) that feeds raw feed material into the digester system 620. The separator 624, long term storage lagoon, and feed pump are or may be conventional and are described herein only to the extent necessary for a complete understanding of the present invention.

As shown in FIG. 9, the seventh example anaerobic digester system 620 comprises a primary digester tank 630 and a secondary or buffer digester tank 632. A primary feed material portion 634a being processed by the example digester system 620 is within the primary digester tank 630 as shown in FIG. 9. The primary feed material portion 634a within the primary digester tank 630 defines a primary feed material level 636a. FIG. 9 also illustrates that a secondary feed material portion 634b is within the secondary digester tank 632, and the secondary feed material portion 634b within the secondary digester tank 632 defines a secondary feed material level 636b. A primary feed material level sensor 638 is arranged within the primary digester tank 630 to determine a level of the primary feed material 634a within the primary digester tank 630.

A first conduit 640 connects the primary digester tank 630 to the secondary digester tank 632. The first conduit 640 is configured to define a primary tank lower opening 650 and a secondary tank lower opening 652. The first conduit 640 is arranged such that the primary tank lower opening 650 and secondary tank lower opening 652 are within the primary and secondary digester tanks 630 and 632 below the primary feed material level 636a and secondary feed material level 636b, respectively. The biogas conduit 622 defines a biogas opening 658 through which biogas passes from the primary digester tank 630 into the biogas conduit 622, and the biogas opening 658 is also above the primary feed material level 636a. Further, for reasons that will be explained in further detail below, the primary tank lower opening 650 is arranged at or near a bottom of the interior of the primary tank 630.

FIG. 9 further illustrates that a flow control valve 660 is arranged to control flow of fluid through the first conduit 640. The flow control valve 660 operates in a closed configuration and at least one open configuration. Typically, the flow control valve 660 may operate in a continuum of open configurations between the closed configuration and a fully open configuration. In the closed configuration, the flow control valve 660 prevents flow of fluid through the first conduit 640. In any open configuration, the flow control valve 660 allows fluid flow between the primary digester tank 630 and the secondary digester tank 632 through the first conduit 640. A pump 670 is configured to force fluid from the secondary digester tank 632 to the separator 624.

FIGS. 9 and 10 illustrate that a bottom wall 680 of the example primary digester tank 630 defines a trough region 682. In particular, the bottom wall 680 comprises inner and outer side walls 684a and 684b and an intermediate wall 686 connecting the inner and outer side walls 684a and 684b. Optionally, a sump 688 may be arranged along at least a portion of the intermediate wall 686 to facilitate draining of the primary digester tank 630.

FIGS. 9 and 10 further illustrate that the example intermediate wall 686 defines a flat, annular shape and is substantially horizontal during normal operation of the seventh example anaerobic digester system 620. The inner side wall 684a takes the form of an inverted frustoconical shape, while the outer side wall 684b takes the form a frustoconical shape of greater diameter than the shape defined by the inner side wall 684a. Solid contaminate, and in particular relatively dense solid contaminate such as sand, that settles to the bottom of the primary digester tank 630 will be directed inwardly by the side walls 684a and 684b and onto the intermediate wall 686, thus further concentrating the solid contaminate at the bottom of the primary digester tank.

FIG. 9 further illustrates that the example first conduit 640 defines a downwardly extending portion 690 that is configured such that the primary tank lower opening 654 is arranged immediately above and directed towards a portion of the intermediate wall 686 and is also arranged between portions of the inner and outer side walls 684a and 684b. The downwardly extending portion 690 of the example first conduit 640 is sized, dimensioned, and arranged to optimize the flow of primary feed material 634a with a higher concentration of solid contaminates out of the primary digester tank 630 when the flow control valve 660 is in its open configuration.

A membrane 692 is arranged within the example primary digester tank 630. The example membrane 692 separates the region of the primary digester tank 630 above the primary feed material level 636a into first and second regions 694 and 696. Biogas created by the digestion process collects in the first region 694, and the biogas opening 658 is in fluid communication with the first region 694. The example membrane 680 is flexible and fluid tight.

The seventh example anaerobic digester system 620 operates generally as follows. The feed pump continuously or periodically pumps the primary feed material 634a into the primary digester tank 630. The primary digester tank 630 is operated in a conventional manner to generate biogas and digestate. Biogas will collect or accumulate within first region 694 and deform the example membrane 692. The biogas is removed from the primary digester tank 630 through the biogas opening and the biogas conduit.

When the primary feed material level sensor 638 determines that the primary feed material level 636a reaches a predetermined value, the flow control valve 660 is placed in an open configuration. The head pressure within the primary digester tank 630 is much greater than the head pressure within the secondary digester tank 632. Accordingly, when the flow control valve 660 is open, a portion of the primary feed material 634a comprising the digestate, liquid material, and solid contaminate (such as sand) flows at a first, relatively high, flow rate from the primary digester tank 630 into the secondary digester tank 632. In particular, a portion of the primary feed material 634*a* flows through the first conduit 640 and the flow control valve 660 and into the secondary digester tank 632 to form the secondary feed material 634*b*. The first conduit 640 and flow control valve 660 are sized, dimensioned, and/or controlled such that the head pressure within the primary digester tank 630 forces a portion of the primary feed material 634*a* from the primary digester tank 630 to the secondary digester tank 632 at the first flow rate (e.g., 6000 gpm) for a short period of time.

The location of the primary tank lower opening 650 is arranged and the first flow rate selected such that the solid contaminate that has accumulated at the bottom of the primary digester tank 630 is flushed out of the primary digester tank 630 along with the digestate and liquid material. Accordingly, the secondary feed material 634*b* within the secondary digester tank 632 typically contains a much higher percentage of solid contaminate than the primary feed material 634*a* within the primary digester tank 630.

The anaerobic digestion process continues to act on the secondary feed material 634*b* in the secondary digester tank 632. At the same time, the secondary feed material 634*b* may be periodically or continuously pumped by the pump 670 out of the secondary digester tank 632 and into the separator 624 at a second, relatively low, flow rate (e.g., 50 gpm). The separator 624 separates the secondary feed material 634*b* into dry solids and liquids. The digestate forms at least a part of the dry solids and may be removed from contaminate and used or otherwise safely disposed of.

Solid contaminate, especially non-digestible, relatively dense solids such as sand, will thus be carried by the intense, short duration flow of feed material from the primary digester tank 630 to the secondary digester tank 632. In particular, non-digestible solids that are more dense than the liquids (primarily water) forming the primary feed material 634*a* will sink to the bottom of the primary digester tank 630 such that such solid contaminates, and especially non-digestible, relatively dense solid contaminates such as sand, are relatively highly concentrated within the bottom of the primary digester tank 630. The primary feed material 634*a* flushed from the primary digester tank 630 and into the secondary digester tank 632 through the first conduit 640 and the flow control valve 660 will thus contain a higher concentration of solid contaminates than the primary feed material 634*a* that remains within the primary digester tank 630.

Accordingly, by periodically removing a small amount of primary feed material 634*a* with a high concentration of solid contaminate, especially non-digestible, relatively dense solids such as sand, from the primary digester tank 630, the primary digester tank 630 is continually cleaned and thus allowed to operate at a relatively high level of efficiency in comparison to a digester system not having a secondary digester tank 632.

Characteristics of the seventh example anaerobic digester system 620 may be the same as those defined above with reference to the first example digester system 20.

What is claimed is:

1. A digester system comprising:
   a primary digester tank containing a primary feed material portion defining a primary feed material level and biogas located within the primary digester tank above the primary feed material level;
   a secondary digester tank containing a secondary feed material portion defining a secondary feed material level and biogas located within the primary digester tank above the primary feed material level;
   a first conduit connected between the primary digester tank and the secondary digester tank to define a primary tank lower opening within the primary digester tank and a secondary digester tank lower opening within the secondary digester tank, where the primary digester tank lower opening is below the primary feed material level and the secondary digester tank lower opening is below the secondary feed material level;
   a second conduit connected between the primary digester tank and the secondary digester tank to define a primary tank upper opening within the primary digester tank and a secondary digester tank upper opening within the secondary digester tank, where the primary digester tank upper opening is above the primary feed material level and the secondary digester tank upper opening is above the secondary feed material level; and
   a flow control valve configured to allow or prevent flow of fluid through the first conduit; wherein
   the second conduit allows flow of biogas directly between the primary digester tank and the secondary digester tank;
   when the flow control valve is configured to allow flow of fluid through the first conduit,
      a portion of the primary feed material portion flows from the primary digester tank to the secondary digester tank to form the secondary feed material portion, and
      when the portion of the primary feed material portion flows from the primary digester tank to the secondary digester tank, biogas flows from the secondary digester tank to the primary digester tank through the second conduit; and
   when the flow control valve is configured to allow flow of fluid through the first conduit, the primary digester tank lower opening is arranged such that solid contaminate that has accumulated at the bottom of the primary digester tank is flushed out of the primary digester tank.

2. A digester system as recited in claim 1, in which, when the flow control valve is configured to allow flow of fluid through the first conduit and the flow control valve is configured to allow flow of fluid through the first conduit, the primary digester tank lower opening is configured such that fluid flows through the first conduit a first flow rate, where the first flow rate is predetermined such that solid contaminate that has accumulated at the bottom of the primary digester tank is flushed out of the primary digester tank.

3. A digester system as recited in claim 1, in which, when the flow control valve is configured to allow flow of fluid through the first conduit and the flow control valve is configured to allow flow of fluid through the first conduit, the primary digester tank lower opening is configured and arranged such that fluid flows through the first conduit a first flow rate and solid contaminate that has accumulated at the bottom of the primary digester tank is flushed out of the primary digester tank.

4. A digester system as recited in claim 1, in which:
   the valve allows the first feed material portion to flow from the primary digester tank to the secondary digester tank at a first flow rate;
   a pump removes the secondary feed material portion from the secondary digester tank at a second flow rate; and
   the first flow rate is greater than the second flow rate.

5. A digester system as recited in claim 1, flow control valve configured to allow flow of fluid through the first conduit when the primary feed material within the primary digester tank exceeds a predetermined level.

6. A digester system as recited in claim 5, further comprising a primary feed material level sensor arranged within the primary digester tank to determine a level of the primary feed material within the primary digester tank.

7. A digester system as recited in claim 1, further comprising a pump configured to remove the secondary feed material portion from the secondary digester tank.

8. A digester system as recited in claim 7, in which the pump is operatively connected to a separator for separating the secondary feed material portion pumped from the secondary digester tank into liquid and solid components.

9. A digester system as recited in claim 1, in which the first conduit comprises a downwardly extending portion arrange to facilitate the flushing of the primary feed material portion at a bottom of the primary digester tank.

10. A digester system as recited in claim 1, further comprising a membrane arranged within the primary digester tank above the primary feed material level to define first and second regions, where the biogas accumulates within the first region.

11. A digester system comprising:
a primary digester tank containing a primary feed material portion defining a primary feed material level and biogas located within the primary digester tank above the primary feed material level;
a secondary digester tank containing a secondary feed material portion defining a secondary feed material level and biogas located within the second digester tank above the secondary feed material level;
a first conduit connected between the primary digester tank and the secondary digester tank to define a primary tank lower opening within the primary digester tank and a secondary digester tank lower opening within the secondary digester tank, where the primary digester tank lower opening is below the primary feed material level and the secondary digester tank lower opening is below the secondary feed material level;
a second conduit connected between the primary digester tank and the secondary digester tank to define a primary tank upper opening within the primary digester tank and a secondary digester tank upper opening within the secondary digester tank, where the primary digester tank upper opening is above the primary feed material level and the secondary digester tank upper opening is above the secondary feed material level;
a flow control valve configured to allow or prevent flow of fluid through the first conduit;
a pump is operatively connected to the secondary digester tank and a separator; wherein
the second conduit allows flow of biogas directly between the primary digester tank and the secondary digester tank;
when the flow control valve is configured to allow flow of fluid through the first conduit,
a portion of the primary feed material portion flows at a first flow rate from the primary digester tank to the secondary digester tank to form the secondary feed material portion, and
when the portion of the primary feed material portion flows from the primary digester tank to the secondary digester tank, biogas flows from the secondary digester tank to the primary digester tank through the second conduit;
the primary digester tank lower opening is arranged such that solid contaminate that has accumulated at the bottom of the primary digester tank is flushed out of the primary digester tank when the flow control valve is configured to allow flow of fluid through the first conduit;
the pump is configured to transfer at least a portion of the secondary feed material portion from the secondary digester tank to the separator at a second flow rate;
the first flow rate is greater than the second flow rate; and
the separator separates the secondary feed material portion pumped from the secondary digester tank into liquid and solid components.

12. A digester system as recited in claim 11, in which the primary digester tank lower opening is configured such that fluid through the first conduit a first flow rate when the flow control valve is configured to allow flow of fluid through the first conduit, where the first flow rate is predetermined such that solid contaminate that has accumulated at the bottom of the primary digester tank is flushed out of the primary digester tank when the flow control valve is configured to allow flow of fluid through the first conduit.

13. A digester system as recited in claim 11, in which the primary digester tank lower opening is configured and arranged such that fluid through the first conduit a first flow rate when the flow control valve is configured to allow flow of fluid through the first conduit and solid contaminate that has accumulated at the bottom of the primary digester tank is flushed out of the primary digester tank when the flow control valve is configured to allow flow of fluid through the first conduit.

14. A digester system as recited in claim 11, further comprising a primary feed material level sensor arranged within the primary digester tank to determine a level of the primary feed material within the primary digester tank, where the flow control valve is configured to allow flow of fluid through the first conduit when the primary feed material level sensor determines that the primary feed material within the primary digester tank exceeds a predetermined level.

* * * * *